(12) United States Patent
Dasbach et al.

(10) Patent No.: US 8,821,452 B2
(45) Date of Patent: Sep. 2, 2014

(54) REMINDER DEVICE FOR A PEN-SHAPED MEDICAL DELIVERY DEVICE

(75) Inventors: Uwe Dasbach, Frankfurt am Main (DE); Irina Lanin, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 109 days.

(21) Appl. No.: 13/389,640

(22) PCT Filed: Aug. 26, 2010

(86) PCT No.: PCT/EP2010/062432
§ 371 (c)(1),
(2), (4) Date: Jun. 24, 2012

(87) PCT Pub. No.: WO2011/023736
PCT Pub. Date: Mar. 3, 2011

(65) Prior Publication Data
US 2013/0226095 A1  Aug. 29, 2013

(30) Foreign Application Priority Data
Aug. 27, 2009  (EP) .................................... 09010974

(51) Int. Cl.
*A61J 7/04* (2006.01)
*A61M 5/315* (2006.01)

(52) U.S. Cl.
CPC ............ *A61M 5/31533* (2013.01); *A61J 7/04* (2013.01); *A61M 2205/6063* (2013.01)
USPC ........................................ 604/189; 206/534

(58) Field of Classification Search
CPC ......... A61J 7/04; A61J 7/0409; A61J 7/0481; A61M 5/31533; A61M 2205/6063
USPC ........................ 604/189; 206/534, 538, 459.5
See application file for complete search history.

(56) References Cited

U.S. PATENT DOCUMENTS

| 3,365,099 | A | | 1/1968 | McTaggart |
| 4,178,071 | A | | 12/1979 | Asbell |
| 4,860,684 | A | * | 8/1989 | Al-Harbi ........................ 116/308 |
| 5,311,688 | A | * | 5/1994 | Aeschbacher et al. ........... 40/665 |
| 5,366,113 | A | * | 11/1994 | Kim et al. ....................... 221/232 |
| 5,482,163 | A | | 1/1996 | Hoffman |
| 5,645,534 | A | * | 7/1997 | Chanoch ........................ 604/189 |
| 2005/0183982 | A1 | * | 8/2005 | Giewercer ..................... 206/534 |

OTHER PUBLICATIONS

Form PCT/IB/326, Notification Concerning Transmittal of International Preliminary Report on Patentability.

* cited by examiner

*Primary Examiner* — Quynh-Nhu H Vu
(74) *Attorney, Agent, or Firm* — McDonnell Boehnen Hulbert & Berghoff LLP

(57) ABSTRACT

Reminder device for indication of time-related information for a pen-shaped medical delivery device, the reminder device comprising:
  a housing part comprising a guiding device,
  an adjusting element which is movably disposed on the guiding device for selecting of a position of the adjusting element for indication of a time information,
  an indication device disposed along the guiding device and having an outer surface with sequential time indicia disposed thereon, wherein the indication device provides a time indication which corresponds to the position of the adjusting element, so that a user can mark a time information on the pen-shaped medical delivery device.

7 Claims, 5 Drawing Sheets

REMINDER DEVICE FOR A PEN-SHAPED MEDICAL DELIVERY DEVICE

CROSS REFERENCE TO RELATED APPLICATIONS

Figure 1:
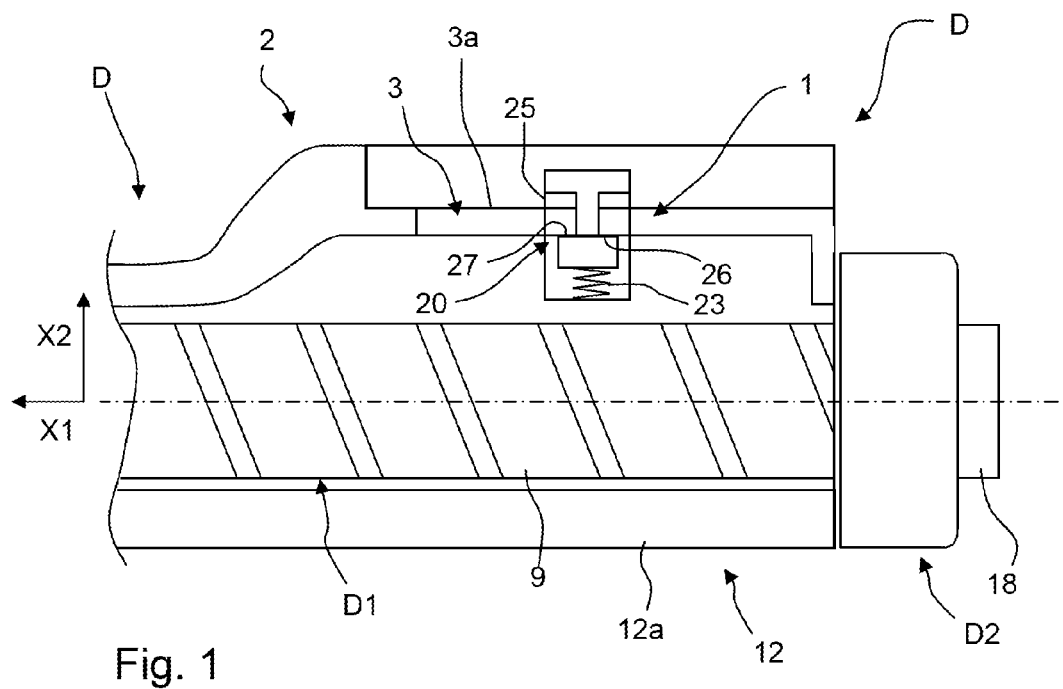

The present application is a 35 U.S.C. 371 National Application of PCT/EP2010/062432 filed Aug. 26, 2010, which claims priority to European Patent Application No. 09010974.5, filed Aug. 27, 2009, the entire contents of which are incorporated entirely herein by reference.

Reminder device for indication of time-related information for a pen-shaped medical delivery device, such a pen-shaped medical delivery device, use of such a medication delivery device and method of manufacturing or assembling such a medication delivery device.

The invention is related to a reminder device for indication of time-related information for a pen-shaped medical delivery device, a use of such a medication delivery device and a method of manufacturing or assembling such a medication delivery device.

From the general state of the art pill dispensers are known having a reminder device to be mounted on a container for pills and serving to provide a reminder of temporary record of the date or time medicine was last taken or next due. For example, U.S. Pat. No. 5,482,163 describes a last indicator apparatus which includes an indicator ring which is disposed over the outer surface of a cylindrical support of a pill dispenser and which is rotatable about the longitudinal axis over the outer surface to each of a plurality of selected positions.

Such indicator apparatus have been considered to be not applicable on pen-shaped medical delivery devices for ergonomic reasons and technical reasons.

An object of the invention is to provide a reminder device which is ergonomically advantageous.

This object is solved according to the features of the independent claims. Further embodiments of the inventions are described in the sub claims referred thereto.

According to one aspect of the invention, a mechanical adjusting device for a pen-shaped medical delivery device is provided. Also, the invention is related to a medical delivery device for dispensing doses of a medicament comprising a mechanical adjusting allowing the user to adjust the time of last usage or time of next dose of the medical delivery device. Such drug delivery devices is applied by persons without formal medical training, i.e., patients, need to administer an accurate and predefined dose of a medicinal product, such as heparin or insulin. In particular, such devices are applied on an irregular basis over a short-term or long-term period. Therefore, a reminder device according to the invention supports the patient to control the time and amount of the medicament to be injected.

According to the invention, a reminder device for a pen-shaped medical delivery device comprising a drive mechanism for dispensing the set dose of the medicament in a distal direction is provided. The reminder device comprises:

a housing part comprising a guiding device. The guiding device may be defined by an axial direction and a radial direction, an adjusting element which is movably disposed on the guiding device for selecting of a position of the adjusting element for indication of a time information, an indication device disposed along the guiding device and having an outer surface with sequential time indicia disposed thereon, wherein the indication device provides a time indication which corresponds to the position of the adjusting element, so that a user can mark a time information on the pen-shaped medical delivery device. According to a preferred embodiment, the reminder device is arranged such that the position of the adjusting element can be selected by the user independently of the operation of the medical delivery device, in particular independently of a dose set or dose delivery operation.

According to a further preferred embodiment, the housing part is part of the housing of a medical delivery device.

According to one embodiment of the invention, the adjusting element is disposed movable on the guiding device in the axial direction. In particular, the guiding device can be formed as guide track on which the adjusting element is movably disposed.

According to a further example of the invention, the reminder device comprises an engaging device for engaging a selected position of the adjusting element, wherein the engaging device comprises a first engaging means positioned on the adjusting element and a second engaging means disposed on the housing part. The adjusting element is movable in a vertical direction with regard to the second engaging means between an engaged and a disengaged position. The engaging device further comprises a biasing means for biasing the first engaging means of the adjusting element against the second engaging means for engaging a selected position of the adjusting element. Particularly, the first engaging means and the second engaging means, each comprises a toothing which is designed such that they are form-fitting in the engaging position of the first engaging means.

According to one example of the invention, the reminder device comprises a cage disposed on the guide track such that it is movable in the axial direction, in that the adjusting element is positioned in the cage and movable with regard to the cage in the vertical direction and wherein the biasing means is positioned between an inner surface of the cage and the positioning means, wherein the second engaging means is positioned on the guide track.

According to an alternative example of the invention, the housing part comprises a housing section and the reminder device comprises an engaging lever pivotally linked to the housing section wherein the second engaging means is positioned on a surface of the engaging lever facing the first engaging means positioned on the adjusting element, in that the biasing means biases the engaging lever in direction to the first engaging means of the adjusting element.

According to the invention, the adjusting element can be disposed on the guiding device such that it can be rotated. Particularly, the guiding device is formed as a circumferential guiding surface on which the adjusting element is rotatable disposed.

The guiding device can be formed as a circumferential recess formed in the housing part in which at least a part of the adjusting means extends wherein the recess comprises the guiding surface.

In these embodiments of the invention, the housing part can particularly be a receptacle holder of the delivery device for storing the medicament. Alternatively, the housing part is a main housing or a cap in which the dose setting means and the dispensing means are integrated.

According to a further example of the invention, the reminder device comprises a engaging device for engaging a selected position of the adjusting element, wherein the engaging device comprises a first engaging means disposed on the adjusting element and a second engaging means disposed on the housing part, in that the adjusting element is rotatable relative to the second engaging means between an engaged and an disengaged position.

According to an example of the invention, the guiding means is formed as a circumferential recess in the housing part in which at least a part of the adjusting means extends and the adjusting element is rotatable relative to the housing means and the reminder device can further comprise a biasing means for biasing the adjusting element or a first engaging means of the adjusting element against the guiding surface or a second engaging means in a engaging position for engaging or for stabilizing a selected position of the adjusting element. In this regard, the first engaging means and the second engaging means each can comprise a toothing which are disposed on surfaces of the adjusting means and of the guiding means resting against each other in the engaging position and which are designed such that they are form-fitting in the engaging position.

According to another example of the invention, the reminder device is designed such that the adjusting element is rotationally disposed on the guiding device and that the housing part which comprises the guiding device is a part of a first housing part and the adjusting element is formed as a further housing part being rotationally coupled to the first housing part of the medical delivery device in an axial direction thereof, wherein the further housing part is in a sliding arrangement with the guiding device. In this regard, the first housing part can be a part of a front housing adapted to receive a receptacle of the medicament to be delivered and being rotationally coupled to the main housing in which the dose setting means and the dispensing means are integrated, wherein the further housing part is formed a ring-shaped member rotationally fixed to the main housing and functioning as the indication device having an outer surface with sequential time indicia disposed thereon. The first housing part can particularly be a part of the main housing.

According to another aspect of the invention, a pen-shaped medical delivery device is provided, comprising:
  a main housing in which a drive mechanism for dispensing a set of a dose of the medicament in a distal direction is disposed,
  a front housing comprising a receptacle for receiving a medicament to be disposed and
  a reminder device, the reminder device according to an example of the invention.

Particularly, the guiding device is disposed on a housing part which is a part of the main housing or of the front housing or the cap and which is defined by an axial direction and a radial direction.

The medication delivery device can be an injector-type device. Further, the medication delivery device can comprise a needle.

According to another aspect of the invention, the use of a medication delivery device according to the invention is provided which is designed for dispensing a medicinal product. The medication delivery device can also be designed for dispensing a pharmaceutical formulation comprising an active compound selected from the group consisting of insulin, growth hormone, low molecular weight heparin, their analogues, and their derivatives.

According to another aspect of the invention, the method of manufacturing or assembling a medication delivery device according to the invention is provided.

A medication delivery device according to instant invention for dispensing a medicinal product is preferably provided for dispensing a pharmaceutical formulation (e.g. solution, suspension etc.) comprising an active compound selected from the group consisting of insulin, growth hormone, low molecular weight heparin, their analogues and their derivatives.

The term "medicinal product", as used herein, preferably means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The term "medical delivery device" or "drug delivery device" according to instant invention shall mean a single-dose or multi-dose or pre-set dose or pre-defined dose, disposable or re-useable device designed to dispense a user selectable or pre-defined dose of a medicinal product, preferably multiple pre-defined doses, e.g. insulin, growth hormones, low molecular weight heparins, and their analogues and/or derivatives etc. Said device may be of any shape, e.g. compact or pen-type. The medication delivery device can be a pen-type device or an injector-type device. Further, the medication delivery device can comprise a needle.

Additionally, said device may contain components designed to monitor physiological properties such as blood glucose levels, etc. Furthermore, the said device may comprise a needle or may be needle-free. In addition, the said device may comprise a fixed needle or a replaceable needle or a moving needle or a shielded moving needle. In particular, the term "drug delivery device" shall mean a disposable needle-based pen-type device providing multiple pre-defined doses having mechanical and manual dose delivery and dose selection mechanisms, which is designed for use by persons without formal medical training such as patients. Preferably, the drug delivery device is of the injector-type.

The medical delivery device comprises a drive mechanism for dispensing a set of a dose of a medicament from a medication receptacle of the delivery device in a distal direction. Dose selection or dose setting for selection or for setting a dose of a liquid or non-liquid medicament in a receptacle may be provided through a dosing mechanism or dose setting means or a dose setting mechanism so that the medical delivery device can further comprise a dose selection mechanism or dose setting mechanism for selection or setting the dose of a liquid medicament in the receptacle to be dispensed by the drive mechanism. The dosing mechanism can partly or totally be realized with components or functions of the drive mechanism or can be realized as a separate mechanism.

The term "distal end" according to instant invention shall mean the end of the device or a component of the device which is closest to the dispensing end of the device. The term "proximal end" according to instant invention shall mean the end of the device or a component of the device which is furthest away from the dispensing end of the device. Accordingly, the "distal direction" is the direction which is directed from the proximal end to the distal end of the device or a component of the device and the "proximal direction" is the direction which is directed from the distal end to the proximal end of the device or a component of the device.

The term "medication receptacle" in the context of the present invention includes a cartridge or receptacle containing the medication as well as a cartridge holder for receiving a cartridge containing the medication. Furthermore, the terms "receptacle" and "cartridge" are exchangeable. This means that by using the term "receptacle", any meaning of the term "cartridge" is included, and vice versa.

The term "receptacle holder" or "cartridge holder" according to instant invention shall mean any component and/or components designed to house a medicament cartridge containing a medication to be delivered by the medication delivery device. Said cartridge holder may be of any shape, e.g. cylindrical or tubular. In general, the cartridge holder may be unitary or a multipart component of a cylindrical tubular or non-tubular shape. It may be made of any suitable material known by a person skilled in the art. Further the cartridge holder is preferably provided with engaging means, e.g. helical threads or part threads or bayonet or the like, on an external and/or internal surface of the distal end and/or proximal end of the cartridge holder designed for engagement with corresponding engaging means located on an exterior and/or interior surface of a housing and/or needle assembly. In a preferred embodiment the cartridge holder is of a unitary tubular design having a part thread located at its proximal end.

Dose delivery may be provided through a mechanical (optionally manual) drive mechanism or drive means or electrical drive mechanism or electro-mechanical mechanism or stored energy drive mechanism, such as a spring, etc. The drive mechanism can in particular comprise a piston being movable in the medication receptacle for displacing the medicament in the receptacle. At the piston a piston rod may be attached, wherein the piston rod is driven by further components of the drive mechanism. The term "piston rod" according to instant invention shall mean a component adapted to operate through/within the housing, designed to translate axial movement (preferably towards the distal end) through/within the medication delivery device, preferably from the drive sleeve to the piston of the cartridge, for the purpose of discharging/dispensing a medication from the cartridge, preferably an injectable product. Said piston rod may be flexible or not. It may be a simple rod, a lead-screw, a rack and pinion system, piston rod, a worm gear system, or the like. The "piston rod" shall further mean a component having a circular or non-circular cross-section. It may be made of any suitable material known by a person skilled in the art.

In one embodiment, the piston rod comprises at least one, more preferably two, external and/or internal helical threads. In another preferred embodiment of the piston rod according to instant invention, a first helical thread is located at a distal end and a second helical thread is located at a proximal end of the said piston rod, whereby the said threads may have the same or, preferably, opposite dispositions. In another preferred embodiment the piston rod of instant invention comprises threads having the same leads at the distal and the proximal end. In yet another preferred embodiment of instant invention the lead of the first helical thread of the piston rod shall be greater than the lead of the second helical thread.

For example, the piston rod may be driven by a "drive sleeve". The term "drive sleeve" according to instant invention shall preferably mean any essentially tubular component of essentially circular cross-section. According to a preferred embodiment of the present invention, the drive sleeve is a component for driving the piston rod in a distal direction for medication delivery. In a preferred embodiment the drive sleeve is engaged with the piston rod. Preferably the drive sleeve comprises an internal thread for engaging an external thread of the piston rod. The drive sleeve is further preferably releasably connected to the dose dial sleeve, most preferably by a clutch means.

The term "dosing mechanism" according to instant invention shall mean any component and/or components and/or assembly designed to allow a user to select and/or set a dose to be dispensed and/or to provide a force necessary to dispense a dose of a medication. Said dosing mechanism can be designed as manual mechanism or electro-mechanical mechanism or electronic mechanism and may be composed of mechanical and/or electro-mechanical and/or electronic components. Additionally, the dosing mechanism may be engaged with the device housing or may be an independent assembly.

For example, the dose setting can be realized by a dose dial sleeve as part of the dosing mechanism. The term "dose dial sleeve" according to instant invention shall preferably mean an essentially tubular component of essentially circular cross-section having either: both an internal and external thread, or an internal thread, or an external thread. The dose dial sleeve can be designed to interact with a drive sleeve. In particular, the dose dial sleeve can be in engagement or coupled with the drive sleeve. For instance, the dose dial sleeve comprises an external thread for engaging an internal thread of the housing or of an insert of the housing. Preferably, the dose dial sleeve according to instant invention comprises an external helical thread having a lead, which is similar to, preferably the same as the lead of an internal helical thread of the drive sleeve. In yet another preferred embodiment the dose dial sleeve is designed to indicate a selected dose of a dispensable product. This may be achieved by use of markings, symbols, numerals, etc., e.g. printed on the external surface of the dose dial sleeve or an odometer, or the like. In a more specific embodiment of instant invention, the dose dial sleeve is provided with a plurality of radially extending members adapted to abut a corresponding plurality of radial stops provided within the housing or an insert of the housing. These radial stop means are preferably provided for stopping the further winding of the dose dial sleeve out of the housing when a dose is set.

The dosing mechanism may be operated by an "operating mechanism" or an "operating device". The term "operating mechanism" or "operating device" according to instant invention shall mean any module or any component or set of components designed to be operated by the user in order to control the drive mechanism. When controlling the drive mechanism, force is transmitted to the drive mechanism. The force can be generated manually or by means of a motor. In a preferred embodiment, the operating device comprises actuating keys. In another preferred embodiment, the operating device comprises a dose dosing sleeve or dose dial sleeve. In order to set of dose or to administer the dose of a medicament, the user actuates the medicament delivery device by means of the operating device. For example, if a user wishes to deliver or expel a medicament from the cartridge, the "operating mechanism" is to be actuated and, for example, an operating button or the "operating mechanism is to be pressed which is a component of the operating device. The operating device is functionally coupled with the drive mechanism. The drive mechanism drives a piston, which is movable within the medicament cartridge (not shown) such that the medicament is expelled from the cartridge.

The term "housing" according to instant invention shall preferably mean any exterior housing ("main housing", "body", "shell") or interior housing ("insert", "inner body") having one or more helical threads. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge, which may be replaceable or non-replaceable, from which a number of doses of a medicinal product may by dispensed. In a more specific embodiment of the instant invention, the housing is provided with a plurality of maximum dose stops adapted to be abutted by a radial and/or axial stop provided on the activation means.

The medicine delivery device can comprise a housing that is formed such that it comprise a first connection part on which a medicament cartridge can be attached, wherein the housing supports the drive mechanism and the operating device, wherein the drive mechanism can act on the medicament cartridge for expelling the medicament from the cartridge.

The housing can comprise two or more separate housing parts. For example, one part can be designed in the form of a housing, wherein another part of the housing can be designed as a removable cap. According to a preferred embodiment, the delivery device comprises a cap removably attachable to the housing for protecting a distal end of the housing, wherein in the present application the "distal end" of the device or a component of the device shall mean the end, which is closest to the dispensing end of the device. The cap can be polished on its outer surface. In one embodiment, the shell of the cap comprises an outer surface of the housing, wherein the outer surface is at least partly polished. Further, the outer surface of the cap can be at least partly coated with a layer of plastic material or a layer of metal. The cap can be at least partly coated with a layer of a ceramic material. According to an embodiment of the invention, the material of the additional ceramic layer of the cap is different from the material of the inner part of the cap made from a ceramic material.

Generally, for the delivery device and/or components or mechanisms thereof an axial direction and a radial direction can be defined. The axial direction corresponds to the longitudinal direction of the delivery device extending in the distal direction of the delivery device.

The term "engaged" according to instant invention shall particularly mean the interlocking of two or more components of the drive mechanism/drug delivery device, e.g. a spline, thread, or meshed teeth connection, preferably the interlocking of helical threads of components ("threadedly engaged").

The term "disengaged" according to instant shall mean the unlocking of two or more components of the dosing mechanism/medication delivery device. Preferably, the term "disengaging" according to instant invention shall mean the unlocking of two or more components of the dosing mechanism/medication delivery device under the force of a biasing means.

The term "coupled" according to instant invention shall mean the connection of two or more components of the drive mechanism/drug delivery device, e.g. using a flange or the like, in which the degree of freedom of the components with respect to each other is limited. In a preferred embodiment one component is permitted to rotate around one axis with respect to another component and is limited from all other rotational and/or translational movement with respect to another component. In a more particular embodiment of instant invention, the drive sleeve is provided with a flange that is coupled to the activation means such that relative rotation about the main longitudinal axis of the drug delivery device is permitted but all other relative movement is essentially prevented.

The term "biasing means" according to instant invention shall preferably mean any component that provides a force on a component and/or components to ensure that the component and/or components are forced together into engagement or forced apart out of engagement. Preferably the biasing means may be manufactured from any suitable flexible force storage material known by a person skilled in the art and may take any suitable form, e.g., a spring.

The invention concerns the use of a medication delivery device according to any of the embodiments described above. The use of the medication delivery device can be provided for dispensing a pharmaceutical formulation comprising an active compound selected from the group consisting of insulin, growth hormone, low molecular weight heparin, their analogues, and their derivatives.

According to the invention, a method of manufacturing or assembling of a medication delivery device according to any of the embodiments described above.

Figure 2:
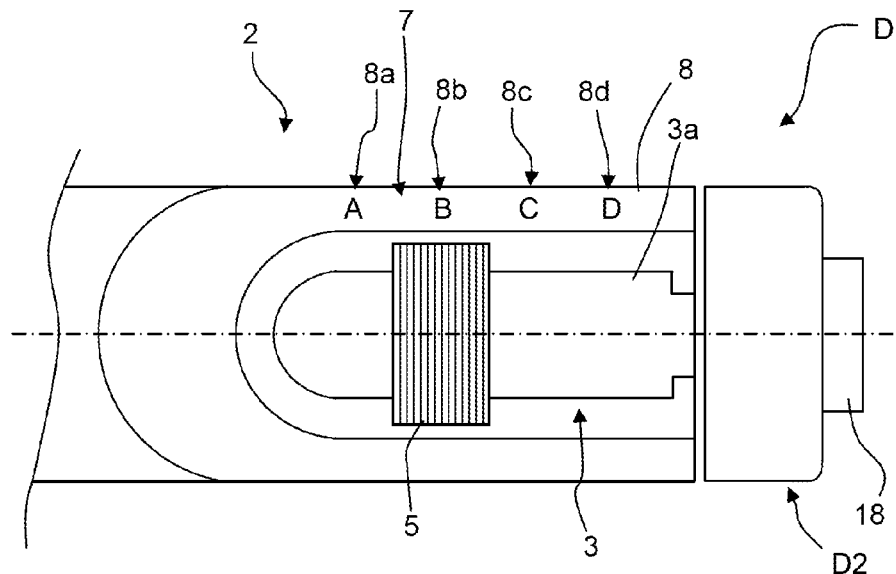
Figure 3:
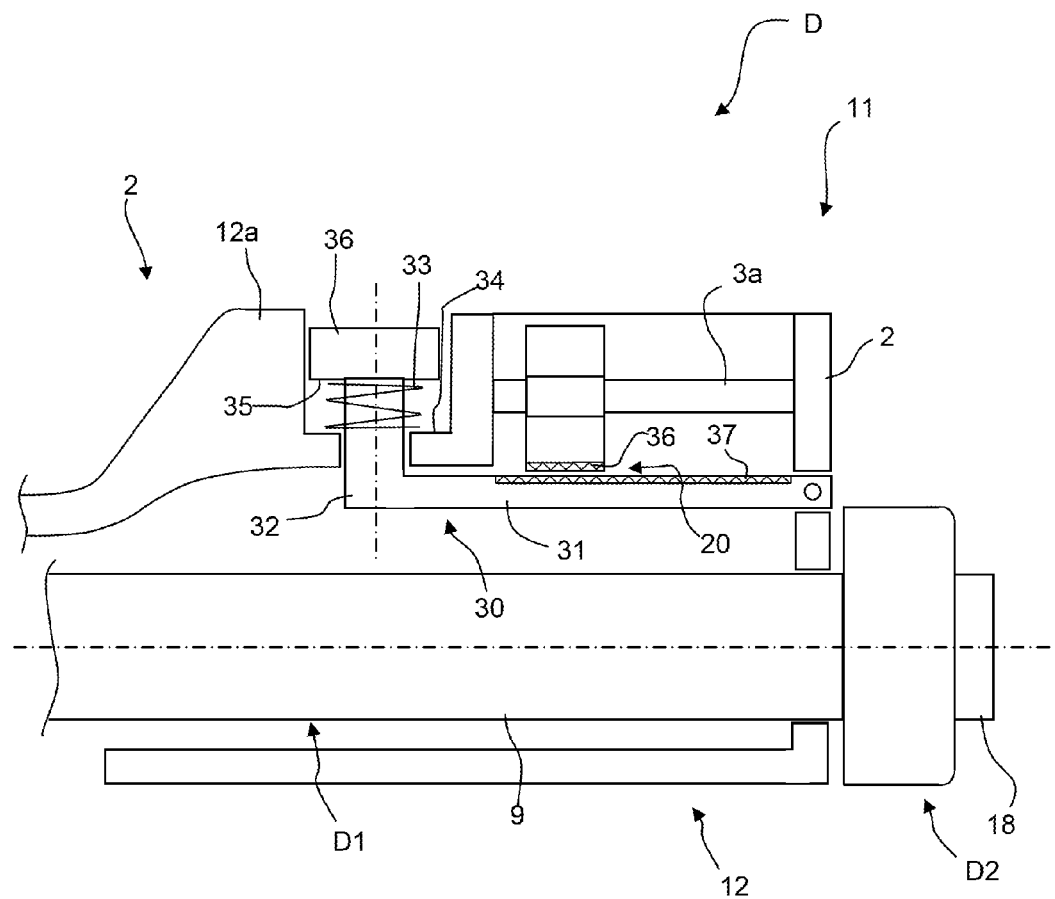
Figure 4:
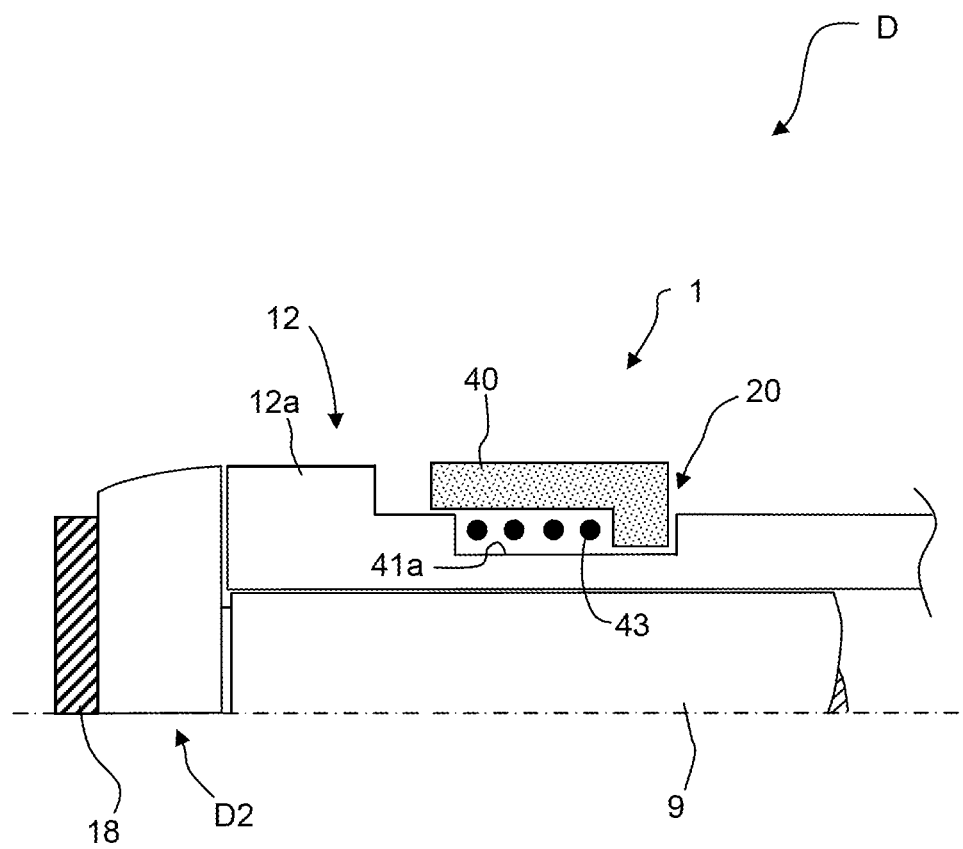
Figure 5:
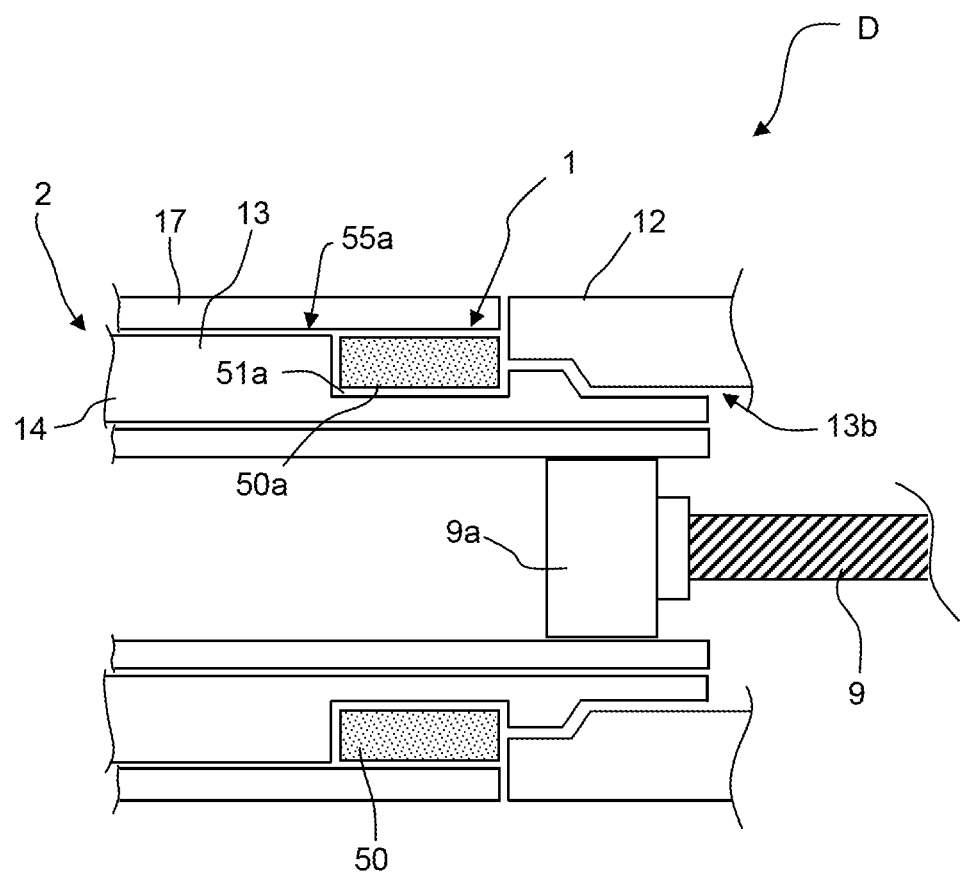
Figure 6:
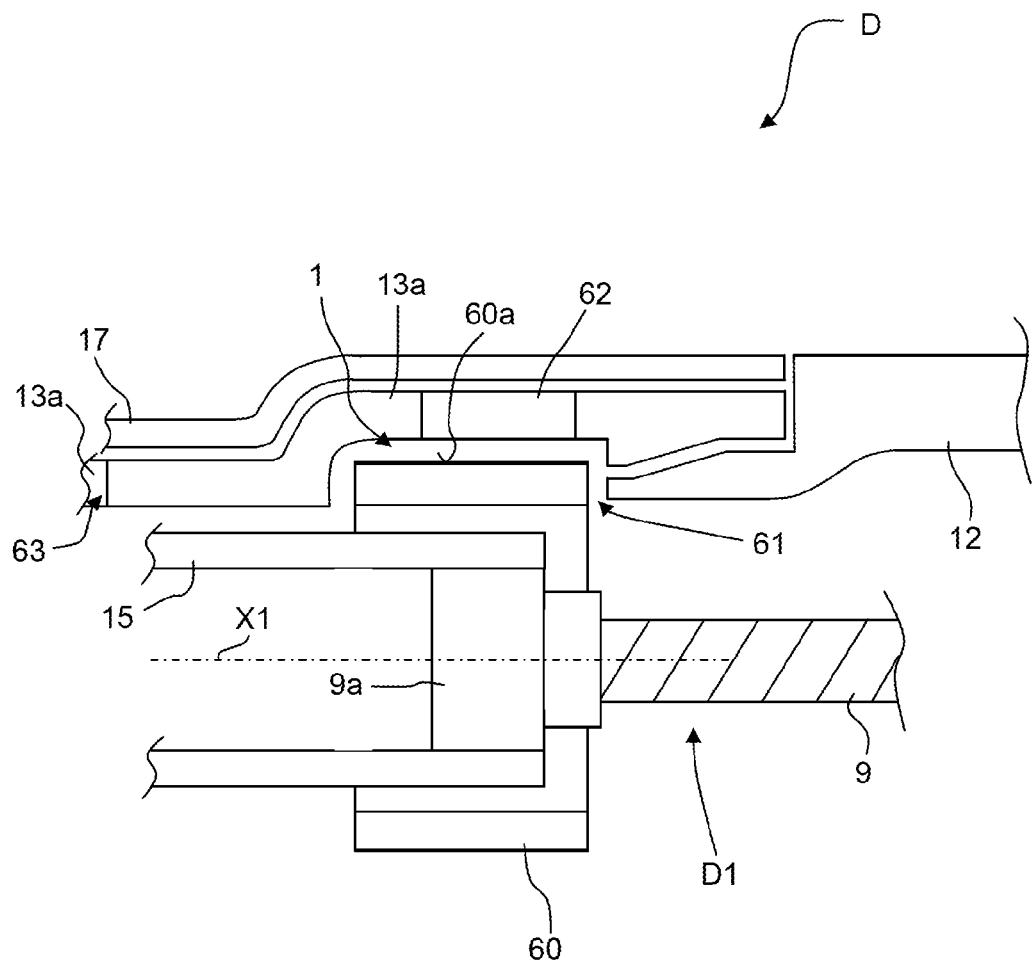

Without any limitation, the instant invention will be explained in greater detail below with reference to the drawings in which:

FIG. 1 is a cross-sectional view of a rear part of a delivery device with a first example of the reminder device comprising an adjusting element which is movable on the guiding device in an axial direction of the delivery device, FIG. 2 is a top view of the reminder device according to the example shown in FIG. 1, FIG. 3 is a cross-sectional view of a rear part of a delivery device with a second example of the reminder device, FIG. 4 is a cross-sectional view of a rear part of a delivery device with a further example of the reminder device comprising an adjusting element which is rotatable disposed on the guiding device of the delivery device, wherein the adjusting element is pre-stressed against the guiding surface for holding a selected position of the adjusting element, FIG. 5 is a cross-sectional view of a rear part of a delivery device with a further example of the reminder device comprising an adjusting element which is rotatable disposed in a circumferential recess formed in the housing part as the guiding device, FIG. 6 is a cross-sectional view of a front part of a delivery device with a further example of the reminder device, showing a ring-shaped member having an indication device on its outer surface is rotationally fixed to the main housing, the adjusting element being a part of a receptacle holder of the delivery device.

In the following detailed description, for components of different embodiments with similar function the same reference numerals may be assigned.

According to the invention a reminder device 1 for mounting on a housing part 2 of a medical delivery device D and a medical delivery device D with such a reminder device is provided. The medical delivery device can particularly be a pen-shaped medical delivery device. The housing part 2 of the medical delivery device D comprises a guiding device 3. For describing the medical delivery device and the reminder device 1 an axial direction X1 and a radial direction X2 can be defined. An adjusting element 5 is movably disposed on the guiding device for selecting of a position of the adjusting element for indication of a time information. Further, an indication device 7 is disposed along the guiding device 3 and having an outer surface 8 with sequential time indicia 8a, 8b, 8c, 8d disposed thereon, wherein the indication device 7 provides a time indication which corresponds to the position of the adjusting element 5, so that a user can mark a time information on the pen-shaped medical delivery device. In FIG. 3 the indicia "A", "B", "C" and "D" are shown which stand as abstract symbols for points of time or periods of time at which a dose has been set or is to be set by the delivery device D. Generally, according to the invention the indication device 7 can have an outer surface 8 with sequential time indicia. As the adjusting element 5 is movable relative to the indication device 7, the adjusting element 5 can in particular be manually disposed in a position, in which the adjusting element 5 or a marking part thereof lies near of a selected time indication for marking a time-information.

The reminder device can be designed such that it can be mounted on a housing or a housing part of the delivery device D.

The medical delivery device D with a reminder device 1 according to the invention or the medical delivery device 10 for which a reminder device 1 according to the invention is to be used can particularly have the design of a pen and can be formed as an insulin pen. The medical delivery device D comprises a housing 11 including a main housing 12 and a front housing 13 (FIG. 5).

In the front housing 13 a receptacle holder or a cartridge holder 14 for holding a medicament receptacle or a medicament cartridge 15 is integrated. In the main housing 12 a drive mechanism D1 comprising a piston rod 9 and optionally a dosing mechanism D2 for setting a dose of a liquid medicament in the receptacle (not shown) can be disposed. The medicament delivery device can also comprise a housing cap 17 for covering the front housing 13.

Further, the medicament delivery device D can include an operating device integrated with the main housing 12. The operating button 18 of an operating device shown in FIG. 1 comprise a rearward circular surface and a annular cone formed surface part which projects from the rear part of the main housing 12, as can be seen from FIG. 1. The outer surface of the operating button 18 further comprises an annular cylindrical part which is adjacent to the cone part shown in FIG. 1 and which extends into the rear part of the main housing 12.

FIG. 1 shows a first embodiment of the reminder device according to the invention. A housing part, in particular a rear or proximal end section 12a of the main housing 12 of the medical delivery device D comprises a guiding device 3 in the form of a guide track 3a extending in the axial direction X1 of the delivery device D. The reminder device further comprises an adjusting element 5 which is movably disposed on the guiding track 3a for selecting of a position of the adjusting element 5 for indication of a time information. The adjusting element 5 can comprise a grip element 5a which is provided on its outer surface when seen from the axial directions X1. An indication device 7 is disposed along the guiding track 3a and has an outer surface 8 with sequential time indicia 8a, 8b, 8c, 8d disposed thereon. Thereby, the indication device 7 provides a time indication which corresponds to the position of the adjusting element, so that a user can mark a time information on the pen-shaped medical delivery device.

The reminder device according to FIGS. 1 and 2 can comprise an engaging device 20 for engaging a selected position of the adjusting element 5, wherein the engaging device comprises a first engaging means (not shown) positioned on the adjusting element 5 and a second engaging means (not shown) disposed on the lower side of the guide track 3a or on the housing part, wherein the engagement means of the adjusting element 5 and of the guide track 3a are formed on corresponding surfaces 26, 27 facing each other. The adjusting element 5 is movable in a vertical direction across the axial direction X1 with regard to the second engaging means between an engaged and a disengaged position. Further, the engaging device 20 further comprises a biasing means 23 for biasing the first engaging means of the adjusting element 5 against the second engaging means for engaging a selected position of the adjusting element 5. The first engaging means and the second engaging means can in particular each comprise a toothing or can have another shape which is designed such that they are form-fitting in the engaging position of the first engaging means. Also, the engaging means can be realized as flat surfaces, optionally having a high friction coefficient.

The reminder device according to FIG. 1 comprises a cage 25 movably disposed on the guide track 3a, wherein the cage 25 is movable in the axial direction X1. The adjusting element 5 is positioned in the cage 25 and movable with regard to the cage 25 in the vertical direction. The biasing means is positioned between an inner surface of the cage 25 and the adjusting element 5.

For changing the position of the adjusting element along the guide device or guide track 3a, the user presses the adjusting element 5 against the radial direction X2 and against the force of the biasing means 23 to disengage the adjusting element 5 from the guide device or guide track 3a.

According to a further embodiment of the reminder device 1 which is shown in FIG. 3, the adjusting element 5 is movable on the guiding device 3 in the axial direction X1 and an engaging lever 30 is pivotally linked to the housing part 2. The engaging lever 30 is designed for interacting with the adjustment element 5 by means of an engagement device 20 with a first and a second engagement means for holding or fixing the same in a selected position on the guiding device 3. The engaging lever 30 can be linked to a distal end 2a housing part 2. The guiding device 3 has the form of a rod on which the adjusting element 5 is glidingly disposed. The engaging lever 30 comprises a first lever part 31 which is linked to a distal end 2a housing part 2 and which extends along the guiding device 3 and a second lever part 32 which protrudes the housing part 2 and which is biased by a biasing means 33 in a direction to the adjusting element 5 for holding or fixing the same in a selected position on the rod. In the embodiment shown in FIG. 3, the biasing means 33 is a spring which is positioned between an outer surface 34 of the housing part 2 and an inner surface 35 of an end piece 36 of the lever 30 which is facing the outer surface 34 of the housing part 2. A surface of the adjusting element 5 which is facing the lever 30 is formed as first engagement means 35 and a surface of the lever 30 which is facing the adjusting element 5 and which is biased against a corresponding surface of the adjusting element 5 is formed as second engaging means 37. The first engaging means 36 and the second engaging means 37 can in particular each comprise a toothing or can have another shape which is designed such that they are form-fitting in the engaging position of the first and second engaging means. Also, the engaging means can optionally be realized as flat surfaces, having a high friction coefficient.

For adjusting the adjusting element 5, the biased engagement lever 30 has to be manually pressed towards the piston rod 9 in order to disengage the lever 30 and the adjusting element 5. In this state, the position of the adjusting element 5 can be changed and a position corresponding to a time indication marked on the indicia device can be selected. This position can be fixed by moving the lever 30 back in its engaged position. This can be achieved by spring means.

As shown in FIGS. 1 and 3, the housing part 2 of the corresponding embodiments of the invention can have a bulged form in the area thereof in which the reminder device 1 is disposed in order to provide space necessary for components of the reminder device 1. Further, the housing part 2 need not be an end section 12a of the main housing 12, but can also be a front or middle section of the main housing 12. Further, the housing part 2 can be a section of the front housing 13.

FIG. 4 shows a reminder device 1 located on a rear section 12a of the main housing 12 which comprises an adjusting element 5 having the form of a ring-shaped member or of a ring 40 which is movable on a guiding device 3 in form of a recess 41 in a rotational direction around the axial direction or the longitudinal axis X1. The recess is formed in the housing part 2 or the main housing 12 and has a bearing surface 41a on which an inner surface 40a of the ring 40 is disposed and rotatable. Further, the ring 40 and the recess 41 are formed such that the ring 40 is axially movable in the axial direction X1 with regard to the recess 41. The ring 40 comprises a first engagement means in form of an engagement surface 40b being directed in the axial direction X1. Correspondingly, the recess 41 comprises an engagement surface 41b facing the engagement surface 40b of the ring 40 having the function of a first engagement means. Between the bearing surface 41a of the recess 41 and the adjusting ring 40 a biasing member in form of a spring 43 is located and designed in order to press the ring 40 against the engagement surface 40b of the recess 41.

The first engaging means 40b and the bearing surface 41b an in particular each comprise a toothing or can have another shape which is designed such that they are form-fitting in the engaging position of the first and second engaging means. Also, the engaging means can be realized as flat surfaces, optionally having a high friction coefficient.

Further, the housing part 2 need not be an end section 12a of the main housing 12, but can also be a front or middle section of the main housing 12. Further, the housing part 2 can be a section of the front housing 13.

For adjusting the ring 40, the biased ring has to be manually pressed away from the engagement surface 41b of the recess 41 in order to disengage the ring 40 and the engagement surface 41b of the recess 41. In this state, the ring 40 can be rotated and a rotational position of a marker (not shown) of the ring 40 corresponding to a time indication marked on the indicia device can be selected. This position can be fixed by releasing the ring 40 so that the ring 40 moves back in its engaged position.

The embodiment according to FIG. 5 comprises a ring-shaped member 50 or ring 50 having the function of the adjusting element 5 being rotationally located in a recess 51 of a housing part 2. In the embodiment of FIG. 5, the housing part 2 is a rear or proximal end section 13a of the front housing 13 of the medical delivery device D. The front housing 13 is coupled with the main housing 12 by coupling means 13b. The front housing 13 also has the function of a receptacle holder or cartridge holder as it includes a receptacle or cartridge 15 in which a piston 9a attached on a piston rod 9 is movably disposed for expelling a medicament from the receptacle.

The ring 50 is disposed on a bearing surface 51a of a recess 51 which is formed in the housing part 2. The ring 50 and the bearing surface 51a are formed such that rotation of the ring 50 is allowed only when a minimum manual force is applied in order to rotate the ring 50. Alternatively, the ring 50 and the recess 51 can be formed such that the ring 50 is axially movable in the axial direction X1 with regard to the recess 51 and that the ring 50 is biased against one surface of the recess 51 being directed in the axial direction, as shown in FIG. 4. According to FIG. 5, the ring 50 comprises a marker (not shown) the position of which can be placed near a time indication on the indicia device which extends on the surface of the housing part 2 in an area 55 lying near the recess 51. For adjusting the ring 50, the ring 50 is to be rotated and a rotational position of a marker (not shown) of the ring 50 corresponding to a time indication marked on the indicia device can be selected.

Ring 50 is secured against rotation by a cap of the medical delivery device D. Rotation of the ring 50 is therefore only possible when the cap is detached.

The embodiment of FIG. 6 shows a reminder device 1 comprising a ring 60 which is rotationally fixed to the main housing 12 by coupling means 61. On the outer surface 60a of the ring 60 and along the circumferential direction thereof a sequence of time-related information is indicated. A rear or proximal end section 13a of the front housing 13 is rotationally coupled to a basic part 13c of the front housing 13 by means of a guiding device 63 in the form of a rotational bearing. The rear end section of the front housing 13 comprises a window 62 positioned above or outside the ring 60 and in an position with regard to the axial direction X1 such that the outer surface 60a time-related information can be seen. In a rotational position of the proximal end section 13a of the front housing 13 the user can see through the window 62 a time-information corresponding to the rotational position of the proximal end section 13a.

Alternatively, the proximal end section 13a can be any part of the housing 11 which is rotationally coupled to the main housing 12 or the front housing 13, wherein a ring with time-information is rotationally fixed with regard to the non-rotational part of the respective housing.

Ring 60 is secured against rotation by a cap of the medical delivery device D. Rotation of the ring 60 is therefore only possible when the cap is detached. This can be achieved, as an advantageous example, by locking means being part of the cap that fit onto or into the window 62.

REFERENCE NUMERALS 1 reminder device
2 housing part
2a distal end
3 guiding device
3a guide track
5 adjusting element
5a grip element
7 indication device
8 outer surface
8a, 8b, 8c, 8d sequential time indicia
9 piston rod
9a piston
10 medical delivery device
11 housing
12 main housing
12a proximal end section/rear section
13 front housing
13a proximal end section
13b coupling means
13c basic part
14 cartridge holder
15 medicament cartridge
17 housing cap
18 operating button
20 engaging device 23 biasing means
25 cage
26, 27 corresponding surfaces
30 engaging lever
31 first lever
32 second lever part
33 biasing means
34 outer surface
35 inner surface/first engagement means
36 end piece/first engaging means
37 second engaging means
40 ring
40a inner surface
40b engagement surface/first engaging menas
41 recess
41a bearing surface
41b engagement surface
43 spring
50 ring-shaped member/ring
51 recess
51a bearing surface
55 area
60 ring
60a outer surface
61 coupling means
62 window
63 guiding device
D medical delivery device
X1 axial direction
X2 radial direction

The invention claimed is:

1. A reminder device for a pen-shaped medical injection device, the medical injection device comprising:
   a cartridge holder;
   a cap removably attachable to the cartridge holder for protecting a distal end of the cartridge holder; and
   a main housing coupled to the cartridge holder, the main housing comprising the reminder device configured to be provided near a proximal end section of the main housing, and
   a drive mechanism for dispensing a user settable dose of the medicament in a distal direction, the drive mechanism comprising a piston rod for acting on a piston of a medication receptacle,
   the reminder device comprising:
   guiding device,
   an adjusting element movably disposed along a surface of the guiding device for the selection of a position of the adjusting element for indication of a time information without the cap attached to the cartridge holder,
   an indication device disposed along the guiding device and having an outer surface with sequential indicia or time indicia disposed thereon,
   wherein the indication device provides a time indication which corresponds to the position of the adjusting element,
   wherein the guiding device comprises a guide track on which the adjusting element is movably disposed in an axial direction, and
   wherein the reminder device further comprises a cage disposed on the guide track such that the cage is movable in the axial direction,
   in that the adjusting element is positioned in the cage and movable with respect to the cage in a vertical direction and
   wherein a biasing element is positioned between an inner surface of the cage and the adjusting element, and
   wherein the position of the adjusting element is user selectable by pressing the adjusting element against a force of the biasing element so as to disengage the adjusting element from the guide track.

2. Reminder device according to claim 1, characterized in that the housing part is a receptacle holder of the injection device for storing the medicament, a main housing in which the dose setting means and/or the dispensing means are integrated, or a cap of the medicament injection device.

3. Reminder device according to claim 1, characterized in that the device is an integral part of the medicament injection device element by a cap of the medicament injection device.

4. Reminder device according to claim 1, characterized in that the device is arranged and configured to be secured against adjustment of the adjusting.

5. Reminder device according to claim 4, characterized in that the reminder device is arranged partially on a receptable holder of the medicament delivery device and in that the adjusting element is arranged such that it is covered by the cap, if the cap is attached to the injection delivery device.

6. Medicament injection device comprising a reminder device according to claim 1.

7. Medicament delivery device according to claim 6, characterized in that the Medicament delivery device comprises a cap, the cap comprising locking means, wherein the reminder device comprises mating locking means which engage with the locking means when the cap is attached to the medicament injection device.

* * * * *